(12) United States Patent
Lange et al.

(10) Patent No.: US 7,426,849 B2
(45) Date of Patent: Sep. 23, 2008

(54) GAS SENSOR FOR DETECTING COMBUSTIBLE GASES

(75) Inventors: Björn Lange, Teschow (DE); Mladen Schlichte, Lübeck (DE)

(73) Assignee: Dräger Safety AG & Co. KGaA, Luebeck (DE)

( * ) Notice: Subject to any disclaimer, the term of this patent is extended or adjusted under 35 U.S.C. 154(b) by 366 days.

(21) Appl. No.: 11/401,945

(22) Filed: Apr. 12, 2006

(65) Prior Publication Data

US 2006/0243029 A1    Nov. 2, 2006

(30) Foreign Application Priority Data

Apr. 30, 2005   (DE) .................. 10 2005 020 131

(51) Int. Cl.
*G01N 7/00*   (2006.01)
(52) U.S. Cl. ...................................... 73/23.2
(58) Field of Classification Search .................. 73/23.2
See application file for complete search history.

(56) References Cited

U.S. PATENT DOCUMENTS

| | | | | |
|---|---|---|---|---|
| RE38,323 E | * | 11/2003 | Sugihara et al. | 435/287.1 |
| RE40,209 E | * | 4/2008 | Sugihara et al. | 435/287.1 |
| 2001/0034479 A1 | * | 10/2001 | Ring et al. | 600/322 |

FOREIGN PATENT DOCUMENTS

| | | |
|---|---|---|
| EP | 0 094 863 | 11/1983 |
| WO | WO 2004/048955 | 6/2004 |

* cited by examiner

*Primary Examiner*—Hezron E. Williams
*Assistant Examiner*—Rodney T Frank
(74) *Attorney, Agent, or Firm*—Walter Ottesen

(57) ABSTRACT

A gas sensor (1) has a pressure-tight sensor housing (4). The sensor housing (4) has a metal plate (5) at its lower end and the metal plate (5) has breakthroughs (6, 7, 8). Metal pins (9, 10, 11) electrically contact the sensor elements (2, 3) and these metal pins are brought to the outside via glass inserts (15, 16, 17).

11 Claims, 1 Drawing Sheet

GAS SENSOR FOR DETECTING COMBUSTIBLE GASES

CROSS REFERENCE TO RELATED APPLICATION

This application claims priority of German patent application no. 10 2005 020 131.8, filed Apr. 30, 2005, the entire content of which is incorporated herein by reference.

BACKGROUND OF THE INVENTION

Gas sensors are used to detect combustible gases and these sensors typically include an electrically-driven measuring element. This measuring element can be an infrared radiator with a detector, a semiconductor element or a catalytic measuring element.

During operation or in the case of a fault, a temperature increase can occur at these measuring elements which basically constitutes the danger of an ignition of the combustible gas mixture to be measured. For this reason, the measuring element is encapsulated in a housing which prevents a possible explosion in the interior of the housing from igniting the ambient surrounding the sensor.

Typically, these explosion-tight housings are of metal. The access of the gas is ensured via a porous material, for example, a wire fabric or metal sinter. This material functions as a flame barrier. To provide an electrical contact of the measuring element from the outside, an opening is provided in the housing through which the cable or metal pins are passed and the opening is closed thereafter with a suitable casting material. Conventional casting materials are, for example, epoxy resin or cement. Typical disadvantages of cast cable passthroughs are inadequate tightness because of separation of the cured cast mass from the housing and a minimum structural size which results from standardization requirements for the thickness of casting material. Thus, and in accordance with present-day standards, the minimum casting thickness is 3 mm for a housing having an interior volume of less than 10 cm and 6 mm for housings less than 100 $cm^3$.

Pressure-tight encapsulated sensors are also known which comprise a metal housing which is embedded in plastic material. Specific minimum casting thicknesses must be maintained even for these housing configurations and complex and costly proof tests must be carried out with respect to maintaining specific standard requirements. In addition, sensor housings with plastic components are not suitable for high temperature applications and for the use in atmospheres containing solvents or acids. A sensor having a plastic housing is described, for example, in international patent publication WO 2004/048955 A2.

A catalytically active gas sensor having a glass passthrough is disclosed in European patent application EP 0 094 863 A1. The catalytically active sensor element is disposed in a sensor housing which is delimited by a porous gas-permeable sinter material. Two metal pins, which contact the sensor element, are passed to the outside through a glass disc at the lower side of the sensor housing. The sensor element is surrounded by zeolite material in order to reduce the energy consumption and increase service life via the insulating action and absorption characteristics of the zeolite material.

The glass passthrough for the metal pins disclosed in European patent application EP 0 094 863 A1 is, however, not suitable for the use in pressure-tight, encapsulated, explosion-protected sensor housings. Sensor housings of this kind must be so dimensioned that they withstand a pressure from 1.5 to four times which can build up in the interior of the sensor housing in the case of an explosion. In addition, it must also be ensured that the housings can withstand explosions in the interior of component assemblies to which the sensor is attached (for example, gas measuring apparatus, electrical terminal boxes, et cetera). With the explosions, pressures of more than several hundred bar can occur.

A flat disc of glass material (that is, a glass disc having a low ratio of thickness to diameter which is, in addition, weakened because of the integration of several metal pins as is the case in known sensor arrangements) will be destroyed by the formation of fissures when subjected to the pressure load occurring in a gas explosion.

SUMMARY OF THE INVENTION

It is an object of the invention to provide a gas sensor having a pressure-tight sensor housing with a gas-tight passthrough for electrical leads or cable.

The gas sensor of the invention is for detecting combustible gases and includes: a plurality of metal pins; a sensor element connected to the metal pins; a piece-wise gas-permeable sensor housing defining an interior and surrounding the sensor element on all sides thereof; a passthrough unit for holding the plurality of metal pins so as to extend into the interior; the passthrough unit including a metal plate having apertures formed therein; a plurality of glass inserts being disposed in corresponding ones of the apertures; and, the plurality of metal pins being fused into the glass inserts.

The advantage of the invention is that the passthrough for the metal pins is configured as a glass passthrough which comprises a massive metal plate having bores in which metal pins are fused tightly into glass. A constructively low thickness of the glass passthrough is sought after here and it has been shown that the required pressure tightness can only be obtained when only one metal pin is seated per bore and glass insert. For the metal disc, which accommodates the glass inserts, the typical diameter lies in a range between 2 and 20 millimeters and lies preferably in a range between 5 to 10 millimeters. The metal plate has breakthroughs corresponding to the number of metal pins which breakthroughs are closed off by the glass inserts.

In an advantageous manner, the glass passthrough is so configured that the materials of glass inserts and metal discs have approximately the same thermal coefficients of expansion. It is practical to oxidize the metal plate and the metal pins in advance of fusing on the glass inserts. The oxide layer effects a gas tight and pressure tight connection between the metal and glass.

Especially good results are obtained with a glass passthrough wherein the selected glass has a lower thermal expansion than the metal so that the metal applies a high pressure to the glass when cooling down and therefore permits a tightness to be achieved up to pressures of several hundred bar. The glass and the metal pin disposed therein are fused at a temperature of approximately 1000° Celsius into the corresponding breakthroughs in the metal plate.

In a further advantageous embodiment, the metal disc of the glass passthrough is joined by a suitable joining process to the remainder of the housing. Here, methods having the possibility of monitoring process parameters can be used such as pulse welding.

BRIEF DESCRIPTION OF THE DRAWING

The invention will now be described with reference to the single figure of the drawing (FIG. 1) which shows, in section, a gas sensor according to an embodiment of the invention.

DESCRIPTION OF THE PREFERRED EMBODIMENTS OF THE INVENTION

Figure 1:
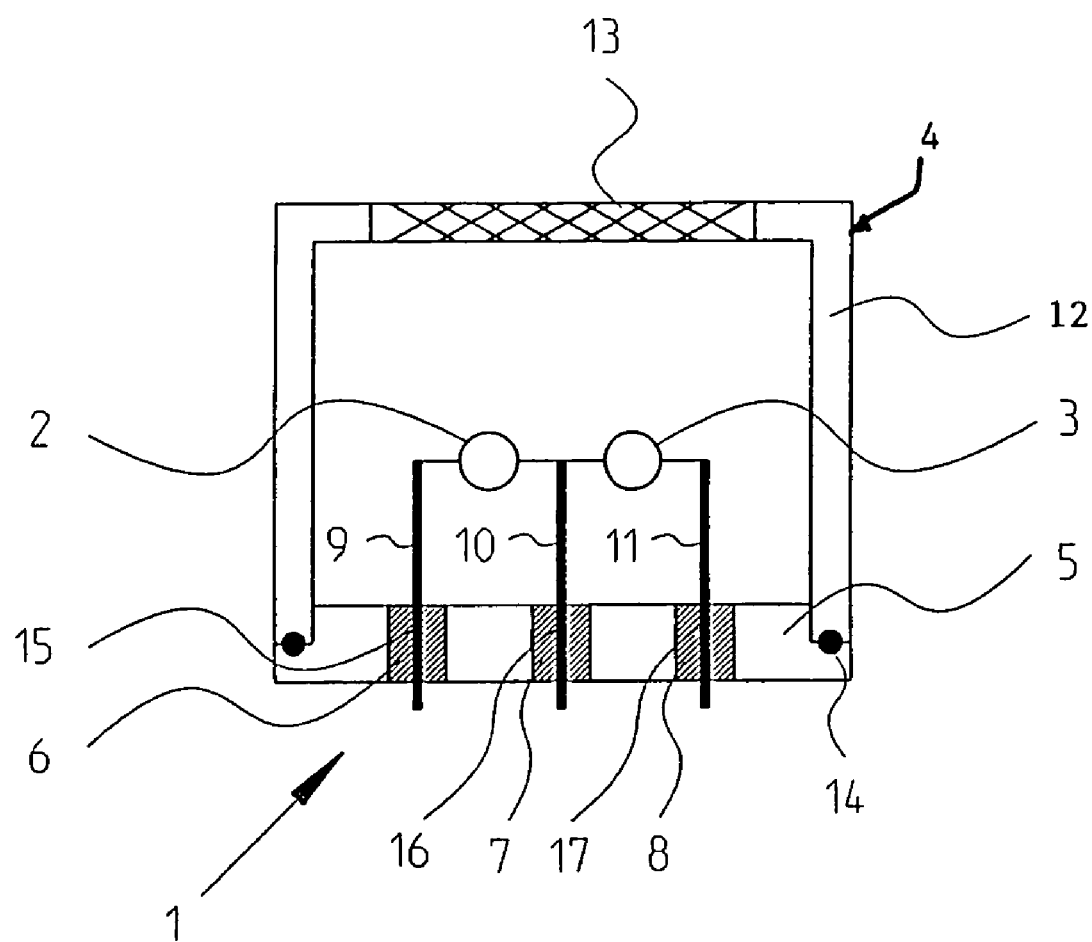

FIG. 1 shows schematically a gas sensor 1 wherein a catalytically active sensor element 2 and a catalytically inactive compensating element 3 are accommodated in a sensor housing 4. The sensor housing 4 comprises a plate 5 made of high-grade steel having breakthroughs (6, 7, 8) for metal pins (9, 10, 11) which contact the sensor element 2 and the compensating element 3. A pot-shaped upper part 12 likewise made of high-grade steel extends from the metal plate 5. The upper part 12 has a gas-permeable sinter disk 13 at its upper end which functions as a barrier to flames. The upper part 12 and the metal plate 5 are joined to each other by a weld seam 14. The breakthroughs (6, 7, 8) are provided with glass inserts (15, 16, 17) which seal the metal pins (9, 10, 11) pressure tight with respect to the metal plate 5. The thickness of the metal plate 5 or the length of the glass inserts (15, 16, 17) is approximately 3 mm.

It is understood that the foregoing description is that of the preferred embodiments of the invention and that various changes and modifications may be made thereto without departing from the spirit and scope of the invention as defined in the appended claims.

What is claimed is:

1. A gas sensor for detecting combustible gases, the gas sensor comprising:
    a plurality of metal pins;
    a sensor element connected to said metal pins;
    a piece-wise gas-permeable sensor housing defining an interior and surrounding said sensor element on all sides thereof;
    a passthrough unit for holding said plurality of metal pins so as to extend into said interior;
    said passthrough unit including a metal plate having apertures formed therein;
    a plurality of glass inserts being disposed in corresponding ones of said apertures; and,
    said plurality of metal pins being fused into said glass inserts.

2. The gas sensor of claim 1, wherein said apertures are bores and only one metal pin is fused in per bore and glass insert.

3. The gas sensor of claim 1, wherein said metal plate, said metal pins and said glass inserts all are made of materials selected to have like coefficients of thermal expansion.

4. The gas sensor of claim 1, wherein the materials of said glass inserts, metal pins and metal plate are so selected that the material of said glass inserts has a lower thermal expansion than said metal pins and said metal plate.

5. The gas sensor of claim 1, wherein said passthrough unit has a thickness which lies in a range of between 0.5 mm and 6 mm.

6. The gas sensor of claim 1, wherein said metal plate has a diameter which lies in a range of between 2 and 20 mm.

7. The gas sensor of claim 1, wherein said metal plate is made of high-quality steel.

8. The gas sensor of claim 1, wherein said metal plate is joined to said sensor housing via one of the following: pulse welding, plasma welding, autogenous welding, soldering, sintering, pressing, gluing or threaded fasteners.

9. The gas sensor of claim 1, wherein said sensor element is an infrared sensor, semiconductor sensor or a catalytic sensor.

10. The gas sensor of claim 1, wherein at least one of said metal plate and said metal pins has an oxide layer.

11. The gas sensor of claim 1, wherein said metal plate and said metal pins each have an oxide layer whereby a gas-tight and pressure-tight connection is provided between the metal and glass.

* * * * *

UNITED STATES PATENT AND TRADEMARK OFFICE
CERTIFICATE OF CORRECTION

PATENT NO.         : 7,426,849 B2  
APPLICATION NO.    : 11/401945  
DATED              : September 23, 2008  
INVENTOR(S)        : Bjoern Lange and Mladen Schlichte Page 1 of 1

It is certified that error appears in the above-identified patent and that said Letters Patent is hereby corrected as shown below:

Column 1:
Line 40: delete "10 cm" and substitute -- 10 $cm^3$ -- therefor.

Signed and Sealed this

Tenth Day of February, 2009

JOHN DOLL  
*Acting Director of the United States Patent and Trademark Office*